United States Patent [19]

Cerami

[11] 4,405,606

[45] Sep. 20, 1983

[54] METHOD FOR ARRESTING FULMINATING INFECTION

[75] Inventor: Anthony Cerami, Flanders, N.J.

[73] Assignee: Evreka, Inc., Bergenfield, N.J.

[21] Appl. No.: 260,144

[22] Filed: May 4, 1981

[51] Int. Cl.³ .......................................... A61K 37/00
[52] U.S. Cl. ................................................. 424/177
[58] Field of Search ...................................... 424/177

[56] References Cited

U.S. PATENT DOCUMENTS 4,137,307 1/1979 Funakoshi et al. ................. 424/177

OTHER PUBLICATIONS

Biological Abstr. 66, 41423.
Graziano, J. H. et al., "The Identification of 2,3-Dihydroxybenzoic Acid as a Potentially Useful Iron-Chelating Drug" J. Pharmacol. Exp. Therap. 190:570–575, 1974.
White, G. P. et al., "The Effect of Chelating Agents on Iron Mobilization in Chang Cell Cultures" Blood 48:923–929, 1976.
Grady, R. W. et al. "Development of New Iron-Chelating Drugs", Part II, J. Pharmacol. & Exper. Therap. 205:757–765, 1978.
Grady, R. W. et al. "The Current Status of Iron Chelation" Ann. Rev. Med. Chem. 13:219–226, 1978.
Hershko, C. et al., "Mechanism of Iron Chelation in the Hypertransfused Rat: Definition of Two Alternative Pathways of Iron Metabolism," J. Lab. Clin. Med. 92:144–151, 1978.
Bhargava, K. K. et al. "New Compounds: $N^1$, $N^8$-bis-(2,3-Dihydroxybenzoyl)-Spermidine and Several Analogues—Potential Iron–Chelating Drugs" J. Pharm. Sci. 69-986–989, 1980.
Jones, R. L. et al. "A Low Molecular Weight Iron Binding Factor from Mammalian Tissue Which Potentiates Bacterial Growth In Vitro and In Vivo" J. of Exp. Med. 151:148–428, 1980.
Pagano, M. et al. "Kinetic Study of the Interaction Between Rat Haptoglobin and Rat Liver Cathepsin B", Can. J. Biochem. 58:410–417, (1980).
Eaton, J. et al., "Haptoglobin: A Natural Bacteriostat", Science, 215:691–693, (1982).
Eaton, J. W. et al. "Haptoglobin Prevents Lethal Hemoglobin-Driven Bacterial Peritonitis" (Abstract submitted to American Society of Hemotology on Sep. 24, 1981).

*Primary Examiner*—Delbert R. Phillips
*Attorney, Agent, or Firm*—David A. Jackson; Daniel H. Bobis

[57] ABSTRACT

A method for arresting fulminating infections of traumatized animal tissue comprises administering to the locus of the tissue trauma an agent capable of binding iron made available to infection-promoting organisms by body fluid released by the trauma. The agent is administered in an amount sufficient to bind all of the available iron, to thereby block the adsorption of the iron by the infection-promoting organisms. The agent preferably comprises one or more binding proteins having known specificity for iron-containing fractions of the body fluid. In particular, the protein haptoglobin may be utilized in the agent to complex with the hemoglobin fraction of blood, to deny access to the iron content by bacterial enzymes. The present method is preferably used in conjunction with existing infection-controlling therapy.

8 Claims, 4 Drawing Figures

METHOD FOR ARRESTING FULMINATING INFECTION

BACKGROUND OF THE INVENTION

1. Field of the Invention

The present invention relates to a method for arresting the development of fulminating infection in traumatized animal tissue.

2. Description of the Prior Art

The adverse pathological consequences of tissue trauma in humans and other animals, including the trauma induced by surgical procedures, has long been studied with a view to preventing the development of bacterial infections that as a rule do not respond well to antibiotic therapy. In particular, trauma and bleeding in the peritoneum of humans, such as results during abdominal surgery, appears to foster the rapid growth of bacteria that cause fulminating infections, that in the majority of cases, are fatal to the patient.

Experimental observations with animal models, suggest that the hemoglobin in blood in responsible for an acceleration in bacterial growth. In particular, the simultaneous intraperitoneal administration of hemoglobin and the bacterium *E. coli* to mice resulted in a fulminating septicemia and rapid death that did not occur when either the bacteria or the homoglobin were individually administered.

Efforts to reduce the occurrence and severity of fulminating bacterial infections, have been limited to the curtailment of unwanted bleeding and the physical removal of unwanted blood from the peritoneal area, in conjunction with the administration of antibiotic therapy. Despite such measures, bacterial infections that develop in this area continue to move rapidly out of control, and frequently are fatal to the patient.

A need therefore exists for a safe and rapid treatment to prevent the fatal spread of bacterial infection in such situations.

SUMMARY OF THE INVENTION

A method of arresting fulminating infections of traumatized animal tissue has been developed, and comprises administering to such tissue at the site of trauma, an agent capable of binding the iron component of the body fluid that has been released by the traumatization of the tissue and thereby made available for adsorption by infection-promoting organisms. The agent is administered in an amount sufficient to bind all of the iron thus available, to render the iron unavailable to the infection-promoting organisms.

The agent of the invention comprises at least one complex-forming protein that is administered in exogenous form, and preferably comprises the protein haptoglobin. In the instance where the body fluid contains iron in the form of hemoglobin, the agent may comprise haptoglobin alone. Where the source of iron includes hemoglobin as well as heme or other iron salts, the agent may include haptoglobin in combination with other binding proteins, such as transferrin or hemopexin, individually and in mixtures with each other.

In the instance of peritoneal trauma, the agent of the present invention may be administered in intraperitoneal fashion in a sterile solution containing the agent in a concentration that may range from about 1.0 to about 100 mg./ml. Direct dosage administration may be utilized, as well as incorporation into conventional irrigation fluids utilized to treat body wounds.

The complex binding proteins of the agent of the present invention are naturally occurring, and may be derived from human plasma, or may be synthetically prepared. The binding proteins are universally compatible with animal tissues and animal body fluids, and the risk of adverse reactions to their administration is non-existent. The present method of treatment is particularly useful in conjunction with current treatment methods employing antibiotic therapy.

Accordingly, it is a principal object of the present invention to provide a method for arresting fulminating infections in traumatized animal body tissues.

It is a further object of the present invention to provide a method as aforesaid that operates in rapid and complete fashion.

It is a yet further object of the present invention to provide a method as aforesaid that operates by forming an irreversible complex with the iron available to infection-promoting organisms.

It is a still further object of the present invention to provide a method as aforesaid which utilizes an agent composed of materials compatible with animal body chemistry.

Other objects and advantages will be apparent to those skilled in the art from consideration of the ensuing description which proceeds with reference to the following illustrative drawings.

DETAILED DESCRIPTION

Figure 1:
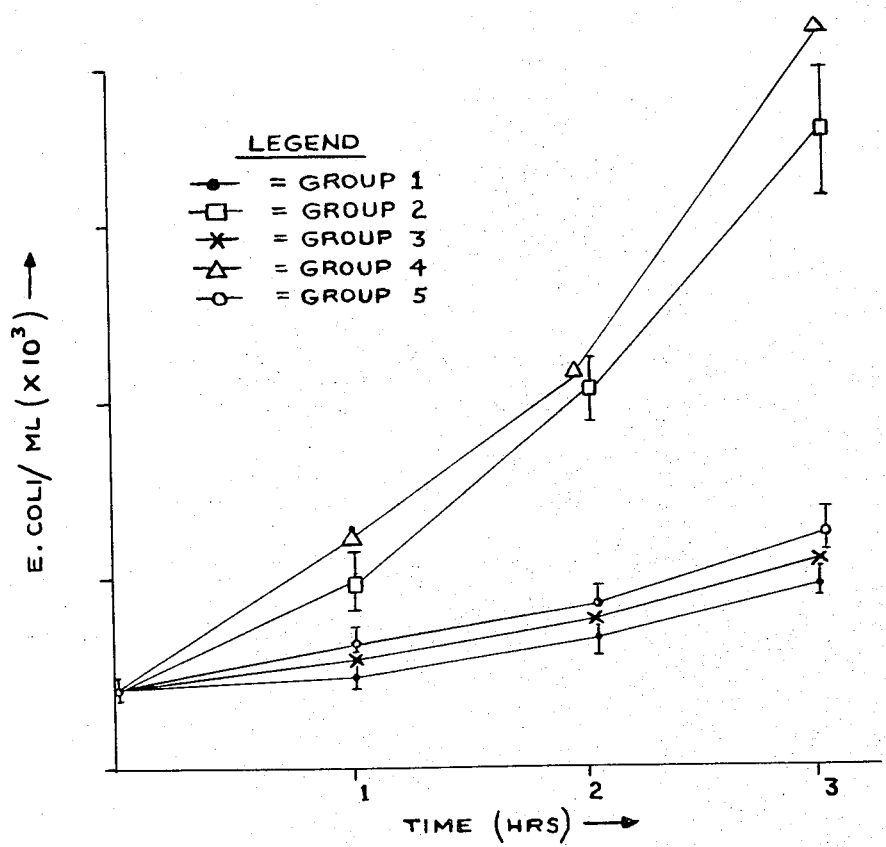
FIGS. 1 and 2 graphically represent the results of in vitro comparative testing of the method of the present invention.

In accordance with the present invention, a method for arresting fulminating infection of traumatized animal tissue is disclosed and comprises administering to such tissue an agent capable of binding iron made available to infection-promoting organisms by body fluid released by the traumatization of the tissue, so as to block the adsorption of the iron by the organisms. The agent is administered in an amount sufficient to bind all of the available iron, which amount is generally proportional to the quantity of released body fluid. The agent preferably comprises at least one complexing protein, and in the instance where the iron containing body fluid comprises the hemoglobin fraction of blood, the agent comprises the protein haptoglobin.

The present invention is predicated upon experimental studies discussed earlier that investigated the relationship between bacterial growth and the presence of blood adjacent the locus of tissue trauma. In particular, it was observed that the hemoglobin fraction of the blood provided a nutrient medium for bacteria that could not be duplicated by administration of other non-iron containing fractions of blood, such as albumin. It was thus concluded that the iron content of the blood fraction served to promote the accelerated growth of the bacteria that defies control by conventional therapeutic techniques.

In particular, it was determined that the bacterial organisms were capable of a form of digestion of the hemoglobin to abstract and thereby adsorb the contained iron; bacterial proteases performed proteolytic clevage of the hemoglobin fraction to abstract the iron component.

Under normal conditions, the iron-containing fractions of the blood are maintained secure against such breakdown by association with certain complexing proteins. In particular, the fraction hemoglobin is secured by association with the protein haptoglobin, while the heme fraction is bound by the protein hemopexin, and iron occurring as iron salts is bound by the protein transferrin. Each of the foregoing binding or complexing proteins, however, is present in relatively small amounts under normal circumstances. Increases of the levels of these proteins can occur gradually, in response to the onset of certain internal pathological conditions, however the body is not equipped to rapidly provide the relatively massive amounts of these proteins necessary to maintain iron in the unavailable sequestered state, in the instance where tissue trauma takes place and the blood is released from the vascular system into the peritoneum and thereby into contact with infection-promoting bacteria. The difficulty engendered by this problem is apparent from a consideration that the red blood cells derived from one 1 milliliter of blood can yield up to 150 milligrams of hemoglobin after proteolytic breakdown, a value far exceeding the capacity of any haptoglobin normally present in that quantity of blood.

With the present method, the agent comprising the complexing protein is derived in exogenous form, and is preferably administered in a sterile solution. The quantity of agent may naturally vary, in relation to the nature and extent of body fluid liberated by the trauma. As the proteins haptoglobin, hemopexin and transferrin exist in human blood in amounts of approximately 1.2 mg./ml., the quantities of such materials administered in accordance with the present method must naturally exceed these amounts substantially, and generally varies in relation to the amount of body fluid released by the trauma, in a ratio with respect thereto ranging up to about 3 to 1. The ratio of the amount of agent administered with respect to body fluid released may preferably range from about 2 to 1 to about 3 to 1. Naturally, the foregoing proportions are provided herein as illustrations only, both of the invention in general, and of a best mode of practice thereof. In instances therefore, where iron content may vary, the proportion of the agent administered with respect to body fluid released, may likewise differ, however such differences are deemed to be within the scope of the present invention.

The agent is preferably utilized in conjunction with conventional antibiotic therapy, and provides the advantage of preventing the acceleration of bacterial growth that has rendered such therapy inadequate in the past. Bacterial growth generally occurs slowly during the initial 24 hours of innoculation, during which time growth is characterized by a lag phase. After this period is surpassed, accelerated or logarithmic growth commences, and full infection of the tissues become pronounced and severe. It is has been found that control of the spread of bacterial infection can be achieved if growth during this initial 24 hour period can be either restrained or reduced in rate.

The agent of the present invention may be administered in a variety of ways; a sterile solution containing the agent may be directly administered by injection or otherwise to the locus of tissue trauma, or may be incorporated in an irrigation fluid utilized to wash body wound areas. The solutions containing the agent may be prepared to a concentration of up to about 100 milligrams per milliliter, and may preferably contain from about 1.0 to about 100 milligrams per milliliter of the agent. The foregoing quantities are illustrative only, as the quantity of agent present in the solutions may vary within the scope of the invention.

The complexing or binding proteins useful in the agent of the present invention include those binding proteins that are naturally occurring in the body fluid, namely haptoglobin, hemopexin and transferrin. In particular, haptoglobin may be utilized alone in the agent, as the majority of tissue trauma results in the release of red blood cells which, after proteolytic breakdown by the enzymes of the bacteria, primarily yield hemoglobin. Haptoglobin is specific in its binding reaction with hemoglobin, and has been observed to form a complex with the hemoglobin that resists the proteolytic breakdown by the enzymes of the bacteria.

In the instance where iron may be present in other fractions of the body fluid or blood, or may exist in a free or salt form, the agent of the present invention may contain other complexing or binding proteins in addition to haptoglobin. Haptoglobin is specifically reactive with hemoglobin, however it is unable to bind other forms of iron, such as heme and iron existing in salt form or the like. Therefore, the present agent may include the proteins hemopexin and transferrin, either alone or in mixtures, in the instance where the additional forms of available iron may exist. For example, such non-bound additional sources of iron may exist in the instance of abdominal surgery, hemorraghic pancreatitis, bacterial peritonitis, and the like. The exact proportions of the respective proteins may vary, however, most instances will require haptoglobin as the primary or major component of the agent. The exact proportion of the respective forms of available iron could be determined by prompt analysis of a sample of the released blood, and the agent could be modified in composition accordingly.

The binding or complexing proteins of the agent of the present invention may be obtained by isolation from human plasma, or may be synthetically prepared by genetic transplant techniques presently known. The exact preparation of the binding proteins of the present invention is within the skill of the art and does not per se form a part of the present invention.

The method of the present invention will be better understood from a consideration of the following examples, illustrating both in vitro and in vivo administration of the agent. All expressions of amounts in percent are intended to refer to percent by weight.

EXAMPLE 1

A large number of synthetic growth media were prepared having a low iron content. The media were thereafter inoculated with equal quantities of the bacteria *E. coli*. Five primary groupings of inocula were developed as follows:
1. Group 1—The bacteria *E. coli* alone.
2. Group 2—*E. coli* and a small amount of hemoglobin (concentration 340 μg/ml.).
3. Group 3—*E. coli*, hemoglobin, as in Group 2., above, and $1.5 \times 10^{-5}$ Molar concentration of haptoglobin purified from human plasma.
4. Group 4—*E. coli*, a small quantity of $10^{-5}$ Molar hemin an $2 \times 10^{-5}$ Molar concentration of haptoglobin.

5. Group 5—*E. coli*, a quantity of $1.5 \times 10^{-5}$ Molar concentration of haptoglobin alone.

In all of the above groupings, the volumetric quantities of hemoglobin, haptoglobin and hemin were roughly equivalent.

Two batteries of such tests were performed, the first of which included all five of the above groupings; the second battery included Groups 1-3 and 5 only. All samples were maintained at a temperature of 37° C., and were observed for a period of time ranging to about 24 hours following inoculation. At the end of the period, bacteria counts of the respective media samples were made, and the results for the first battery of tests were tabulated and set forth in FIG. 1, while the test results for the second battery of tests are set forth in FIG. 2.

The data from the respective groupings is identified by the corresponding graphical symbol set forth in the legends accompanying each Figure. The data points plotted in FIG. 1 represent the respective mean and standard deviation values determined from a comparison of three samples of each grouping observed and counted at the indicated time interval.

Referring to FIG. 1, the rate of growth of the bacteria *E. coli*, alone can be seen to be relatively flat, so that the initial or lag phase of bacterial growth is apparent. By contrast, the addition of the hemoglobin to the growth medium alone results in a dramatic acceleration in bacterial growth. This growth, however, is neutralized in the instance of Group 3, wherein a comparable quantity of haptoglobin is introduced together with the hemoglobin, and is similar in rate to the growth pattern of the bacteria inoculated with haptoglobin alone. Finally, the results of the Group 4 media illustrates the specificity of haptoglobin for hemoglobin. In these samples, haptoglobin was introduced, however hemin, containing a variant form of available iron was provided in place of hemoglobin. Haptoglobin proved ineffective in this instance, and greatly accelerated growth of the bacteria was in evidence.

Figure 2:
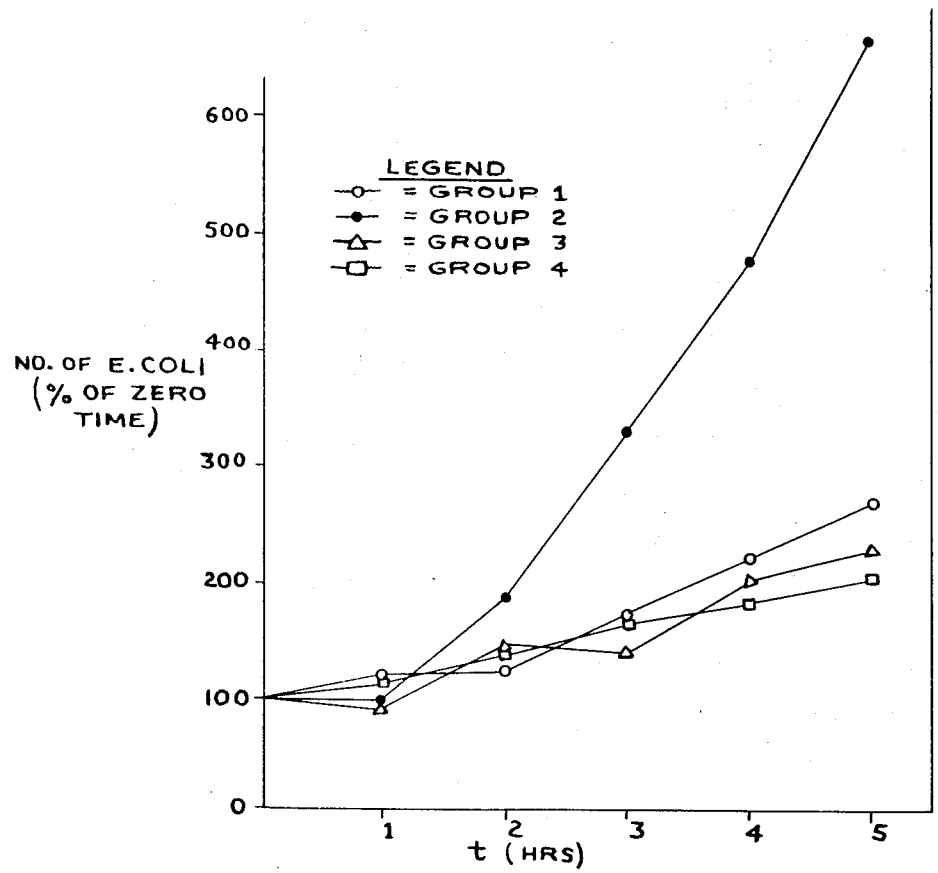

The data gathered from the first battery of tests was corroborated by further testing, shown in FIG. 2. In similar fashion to FIG. 1, the media containing the bacteria alone exhibited a relatively flat growth curve, while the media bearing the added hemoglobin exhibited a dramatic increase in the rate of bacterial growth within two hours.

The addition of a quantity of haptoglobin to the inoculum containing hemoglobin, shown in Group 3, appeared to neutralize the effects of the hemoglobin, so that the bacteria exhibited a growth rate that was, in fact, even flatter than the rate observed for the bacteria alone. Similarly, the growth rate for Group 5, where haptoglobin alone was added, proved flatter than that of the control Group 1.

The foregoing in vitro studies confirmed the specific effect that haptoglobin has upon bacterial growth in the presence of hemoglobin, and prompted the in vivo studies that are discussed below.

EXAMPLE 2

In vivo studies were conducted to determine the efficacy of the present method. A total of 30 laboratory rats were divided into three groups, and were innoculated with intraperitoneal injections as set forth below.

1. Group 1—These rats were innoculated with $2 \times 10^9$ *E. coli* bacteria alone.
2. Group 2—These rats were injected with $2 \times 10^9$ *E. coli* together with 10 mg. stroma-free hemoglobin.
3. Group 3—These rats received $2 \times 10^9$ *E. coli*, 10 mg. stroma-free hemoglogin and 20 mg. purified human haptoglobin (the quantity of haptoglobin estimated by its binding capacity).

The bacteria utilized in this test were isolated from a fatal human case of septicemia. After injection, the rats were placed under observation for a period of 72 hours, to note the adverse effect, if any, caused by the respective injections. The rats were regularly observed during this period, and the results regarding survival were gathered and are presented in graphical form in FIG. 3. The identity of the results of the respective groups may be determined from the legends accompanying the graph.

Figure 3:
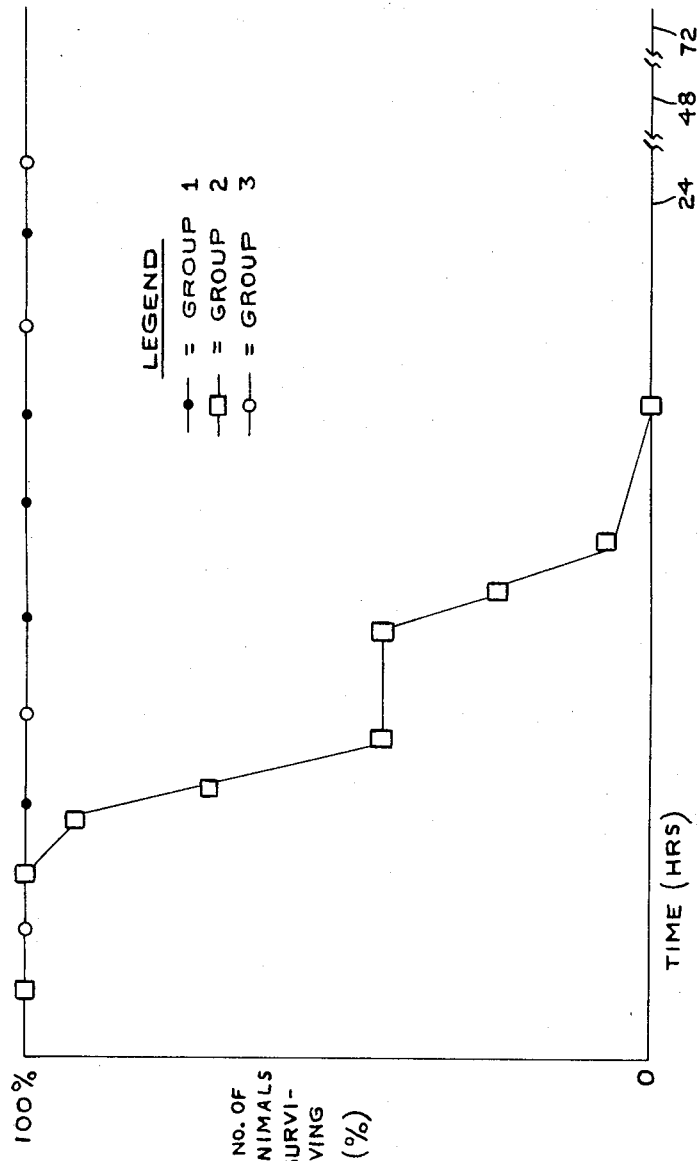
FIGS. 3 and 4 graphically represent the results of in vivo testing of the method of the present invention.

It is apparent from FIG. 3, that the Group 1 subjects were able to successfully fend off the lethal effects of the bacteria alone, as administered in the Group 1 tests. By contrast, however, the introduction of hemoglobin to the inoculum, resulted in the death of all of the rats from overwhelming septicemia within 24 hours after injection.

The inclusion of haptoglobin in Group 3 appeared to counteract the lethal effects of the hemoglobin, as all of the rats in this grouping survived the entire test period.

The results of this example illustrates that haptoglobin exerts a neutralizing affect upon hemoglobin in the presence of bacteria in an in vivo situation.

EXAMPLE 3

Additional in vivo testing was conducted with laboratory rats in a manner similar to that set forth in Example 2 above. Two batteries of tests were conducted, each battery differing only in the number of rats utilized, and the specific composition of the innocula.

In the first battery of tests, three groups each of seven male rats, each averaging in weight between 125 and 150 gms., were injected with a 1.25 ml. volume of individual preparations set forth according to group numbers, below.

1. Group 1—Inoculum comprised 20 mg. stroma-free hemoglobin (SFHb) (3.4 g %), $2.5 \times 10^7$ *E. coli* bacteria and 66.7 mg. Albumin.
2. Group 2—Inoculum comprised $2.5 \times 10^7$ *E. coli* and 86.7 mg. Albumin, alone.
3. Group 3—Inoculum comprised $2.5 \times 10^7$ *E. coli* bacteria, 20 mg. stroma-free hemoglobin (SFHb) (3.4 g %) and sufficient haptoglobin to bind 20 mg. hemoglobin (HbBC=30 mg./ml.) (equivalent to approximately 67 mg. of protein).

The second battery of tests were performed with three groups of eight rats each, the rats otherwise identical to those utilized in the first battery of testing. The inocula utilized in the second battery of tests are set forth below.

1. Group 4—The Inoculum comprised 20 mg. stroma-free hemoglobin (SFHb) (3.4 g %), $2.5 \times 10^7$ *E. coli* bacteria and 66.7 mg. Albumin.
2. Group 5—Inoculum comprised $2.5 \times 10^7$ *E. coli* and 86.6 mg. Albumin, alone.
3. Group 6—Inoculum comprised $2.5 \times 10^7$ *E. coli* bacteria, 20 mg. stroma-free hemoglobin (SFHb) (3.4 g %) and sufficient haptoglobin to bind 20 mg. hemoglobin (HbBC=19 mg./ml.) (equivalent to approximately 66.7 mg. of protein).

All of the animal subjects were given intraperitineal injections that contained hemoglobin and haptoglobin in premixture. After administration of the injections, the rats were placed under study for a period of 72 hours, and mortality of the rats was observed at 24 hour intervals. The results of this experiment are set forth in Tables I and II, and are graphically presented in FIG. 4.

TABLE I

RAT MORTALITY AFTER 48 HOURS

| GROUP NO. | MORTALITY | |
|---|---|---|
| | No. Dead | Total No. Tested |
| 1 | 6 | 7 |
| 2 | 1 | 7 |
| 3 | 0 | 7 |
| 4 | 6 | 8 |
| 5 | 0 | 8 |
| 6 | 0 | 8 |

TABLE II

SUMMARY - TABLE I DATA

| INOCULUM | MORTALITY | |
|---|---|---|
| | No. Dead | Total No. Tested |
| E. coli alone | 1 | 15 |
| E. coli plus hemoglobin | 12 | 15 |
| E. coli, hemoglobin plus haptoglobin | 0 | 15 |

Figure 4:
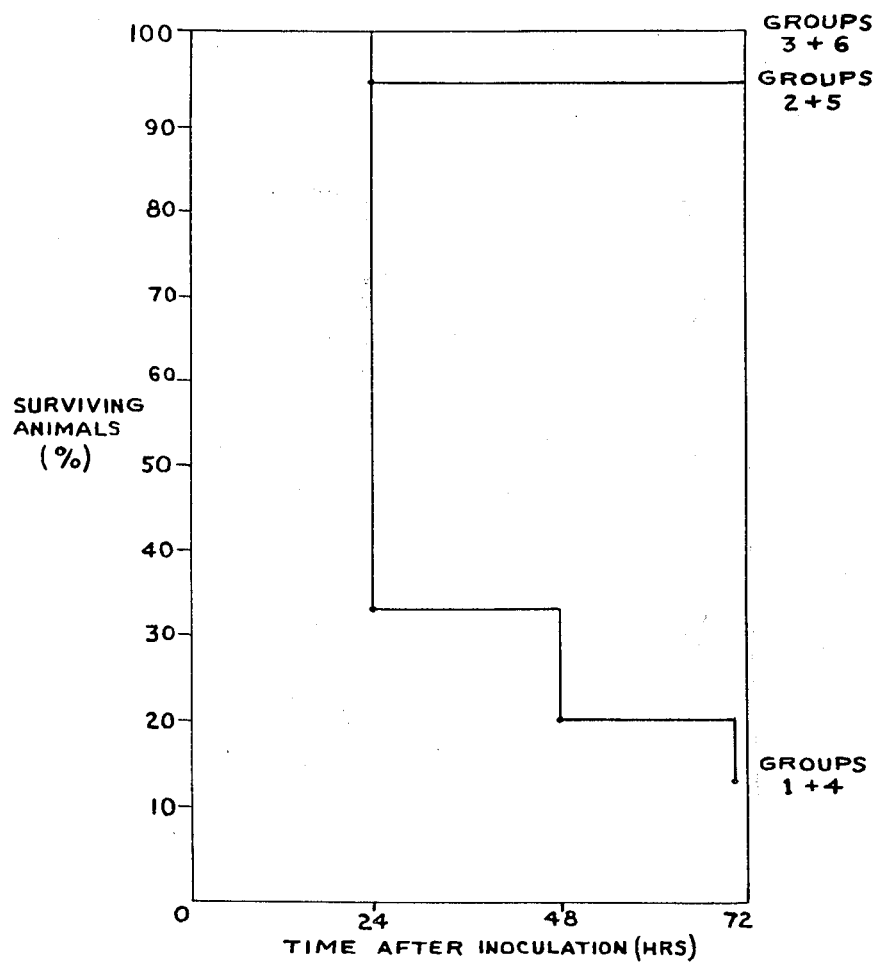

A review of FIG. 4 graphically confirms the results set forth in Table II, above. The rats inoculated with either the bacteria alone or the bacteria containing both hemoglobin and haptoglobin, were generally successfully resistant to fatal infection; of a total number of 30 rats tested in these two groups, only 1 rat administered E. coli alone died.

By contrast, the rats to which the inoculum including E. coli and hemoglobin was administered, suffered heavy mortality, with the heaviest death rate occurring within the first 24 hours after inoculation. During this first period, 10 out of the 15 rats died, after 48 hours 12 out of 15 rats had died, while after 72 hours a total of 13 rats were dead. These tests further confirm the effacacy of haptoglobin in neutralizing the growth accelerating effect of hemoglobin in contact with bacteria in the peritoneal environment.

The present method is particularly useful in conjunction with conventional antibiotic therapy to control and eliminate infections that arise adjacent traumatized animal tissue. The present method serves only to prevent the uncontrolled development of the infection, to permit the conventional therapy as well as the body defenses to develop an effective counter-attack to the spreading infection.

This invention may be embodied in other forms or carried out in other ways without departing from the spirit or essential characteristics thereof. The present invention is therefore to be considered as in all respects illustrative and not restrictive, the scope of the invention being indicated by the appended claims, and all changes which come within the meaning and range of equivalency are intended to be embraced therein.

What is claimed is:

1. A method for arresting fulminating infection of traumatized tissue in animals comprising administering to said tissue an agent capable of binding iron made available to infection-promoting organisms by body fluid released by the traumatization of said tissue, said agent administered in an amount sufficient to bind all of said available iron, and thereby to block the adsorption of said iron by said organisms,
   wherein said agent comprises at least one complexing protein, and said complexing protein comprises haptoglobin.

2. The method of claim 1 wherein said complexing protein comprises haptoglobin and a material selected from the group consisting of transferrin, hemopexin and mixtures thereof.

3. The method of either of claims 1 or 2 wherein said agent is disposed in a sterile solution.

4. The method of claim 3 wherein said sterile solution contains from about 1.0 to about 100 mg./ml. of said agent.

5. The method of either of claims 1 or 2 wherein said agent is directly administered at the locus of said traumatization.

6. The method of either of claims 1 or 2 wherein said agent is added to an irrigation fluid utilized at the locus of a tissue wound.

7. The method of either of claims 1 or 2 wherein said agent is administered at a ratio with respect to said body fluid of up to about 3:1.

8. The method of claim 7 wherein said ratio ranges from about 2:1 to about 3:1.

* * * * *